United States Patent [19]
Premchandran et al.

[11] Patent Number: 5,922,849
[45] Date of Patent: Jul. 13, 1999

[54] PROCESS FOR PREPARATION OF N-DEMETHYL-4"-DEOXY-ERTHROMYCINS A AND B

[75] Inventors: Ramiya H. Premchandran, Gurnee; Albert V. Thomas, Vernon Hills, both of Ill.; Juliette K. Busse, San Diego, Calif.; John E. Dete, Waukegan, Ill.

[73] Assignee: Abbott Laboratories, Abbott Park, Ill.

[21] Appl. No.: 08/754,867

[22] Filed: Nov. 22, 1996

[51] Int. Cl.$^6$ .................................................. C07H 1/00
[52] U.S. Cl. .................................. 536/7.2; 536/18.5
[58] Field of Search ...................... 536/7.2, 18.5

[56] References Cited

U.S. PATENT DOCUMENTS 3,725,385  4/1973  Freiberg ..................... 536/7.2

FOREIGN PATENT DOCUMENTS 9313780  7/1993  WIPO .

OTHER PUBLICATIONS

Synthesis of 4"–Deoxy Motilides: Identification of a Potent and Orally Active Prokinetic Drug Candidate, P. Lartey et al., *Journal of Medicinal Chemistry*, vol. 38, No. 10, pp. 1793–1798 (1995).

*Primary Examiner*—Elli Peselev
*Attorney, Agent, or Firm*—Mona Anand

[57] ABSTRACT

A process for the preparation of N-demethyl-4"-deoxy-erythromycins A and B, having the formula:

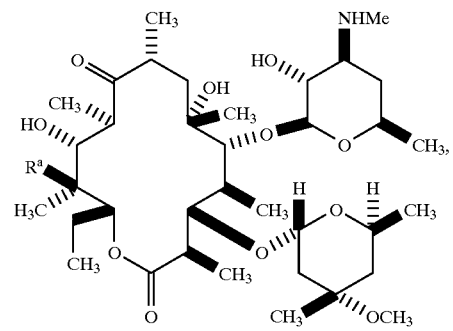

wherein $R^a$ is H or OH, by stepwise addition of iodine and base to the N-dimethyl-4"-deoxyerythromycin, preferably, accompanied by sparging with an inert gas.

21 Claims, No Drawings

PROCESS FOR PREPARATION OF N-DEMETHYL-4"-DEOXY-ERTHROMYCINS A AND B

TECHNICAL FIELD

The present invention relates to a process for the preparation of N-demethyl-4"-deoxy-erythromycins A and B, which have uses as an intermediate in the preparation of the gastrointestinal prokinetic agent compounds.

BACKGROUND OF THE INVENTION

Erythromycins A through D, represented by formula (E),

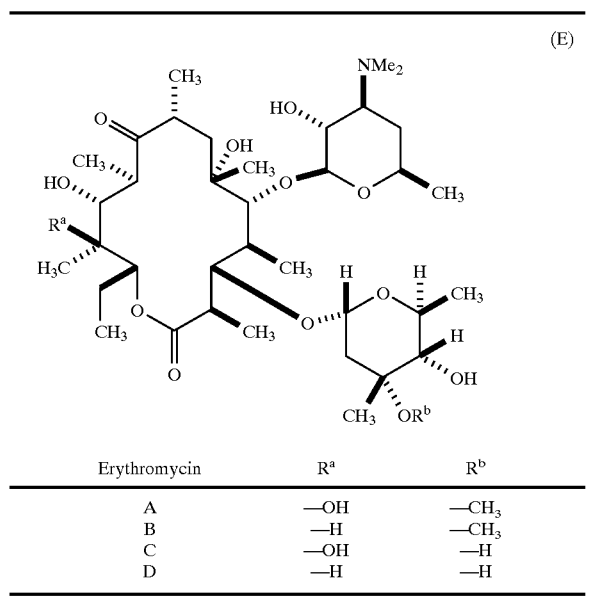

| Erythromycin | $R^a$ | $R^b$ |
| --- | --- | --- |
| A | —OH | —$CH_3$ |
| B | —H | —$CH_3$ |
| C | —OH | —H |
| D | —H | —H | are well-known and potent antibacterial agents, used widely to treat and prevent bacterial infection.

Some erythromycin derivatives have use as prokinetic agents. For example, an erythromycin B derivative, having the formula:

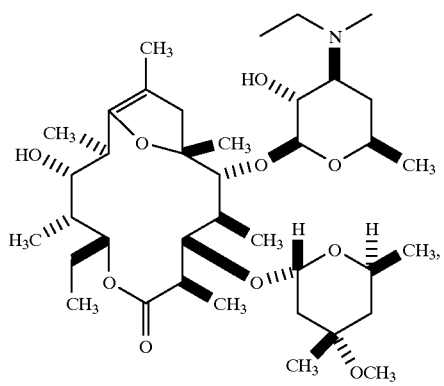

has been described as a prokinetic agent having use in the treatment of gastrointestinal motility disorders (see P. A. Lartey et al., *J. Med. Chem.*, 38 (1793–1798 (1995); and R. Faghih, et al., PCT application WO 9313780, published Jul. 22, 1993).

The preparation of these prokinetic compounds requires the preparation of the intermediate compounds, N-demethyl-4"-deoxy-erythromycin A and N-demethyl-4"-deoxy-erythromycin B. More efficient methods of preparation of these compounds are needed to ensure more efficient synthesis and wider availability of the desired prokinetic agents.

One procedure for the preparation of N-demethyl derivatives of various macrolide antibiotics has been described in U.S. Pat. No. 3,725,385, issued Apr. 3, 1973, which teaches that the methyl group may be removed by a one-step treatment with a single addition of iodine in a pH-adjusted solution at from −10° C. to 50° C.

SUMMARY OF THE INVENTION

The present invention provides a more efficient process for the preparation of N-demethyl-4"-deoxy-erythromycins A and B. The process comprises stepwise additions of iodine in a pH-adjusted solution at from 40° C. to 70° C., and preferably at 50° C. to 60° C. These N-demethyl-4"-deoxy-erythromycins A and B have utility as intermediates in the preparation of desired prokinetic agents.

One aspect of the present invention relates to a two-stage process for the preparation of N-demethyl-4"-deoxy-erythromycins A and B, having the formula:

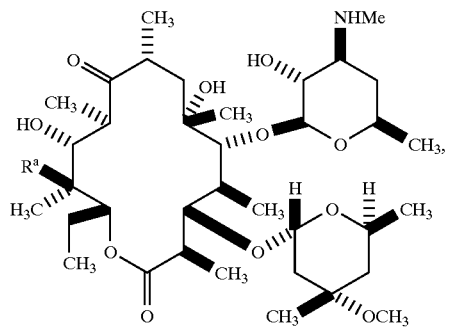

wherein Ra is H or OH, comprising:

(a) treating a compound having the formula:

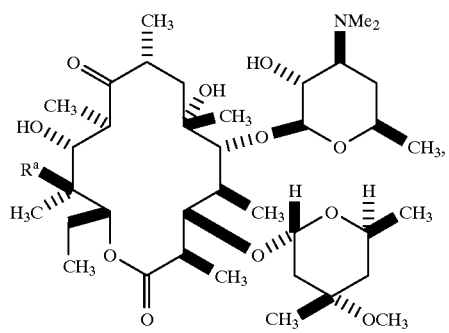

wherein $R^a$ is H or OH, in a solution of sodium acetate with stepwise addition, respectively, of iodine and aqueous base in amounts sufficient to maintain a pH of 8–9 in the reaction mixture and stirring until the iodine color disappears, (b) isolating a crude reaction product; and (c) treating the crude reaction product of step (b) in accordance with the step (a) above, and isolating the final product.

Another aspect of the present invention relates to a one-stage process for the preparation of N-demethyl-4"-deoxy-erythromycins A and B, having the formula:

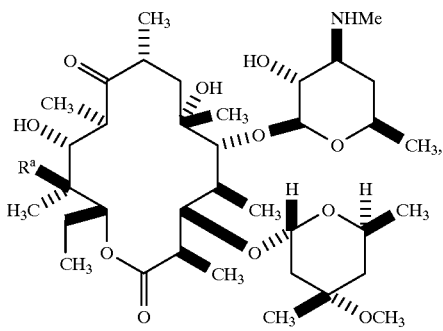

wherein $R^a$ is H or OH, comprising:

(a) treating a compound having the formula:

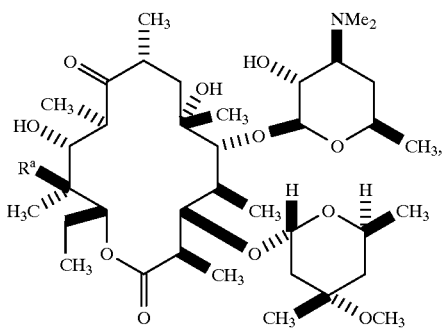

wherein $R^a$ is H or OH, in a solution of sodium acetate accompanied by sparging of the solution with an inert gas, with stepwise addition, respectively, of iodine followed by addition of aqueous base in amounts sufficient to maintain a pH of 8–9 in the reaction mixture and stirring until the iodine color disappears; and (b) isolating the desired product.

The process of the invention provides efficient and improved methods for preparing the intermediate compounds, which are useful in the synthesis of prokinetic agents.

DETAILED DESCRIPTION OF THE INVENTION

The process of the invention involves demethylation of one of the methyl groups of the N-dimethyl group of the desosamine portion of the erythromycin compounds. In particular, it involves the demethylation of the N-dimethyl group of the 4"-deoxy-erythromycins A and B. The 4'-deoxyerythromycin starting material compounds are available from Abbott Laboratories.

The process of the invention as illustrated in Scheme 1 may be a one-stage or a two-stage process in which a starting material 4"-deoxyerythromycin compound is treated in solution with iodine in the presence of sodium acetate at a pH of 8–9 with additions of aqueous base as necessary to maintain the pH in the desired range. Both the iodine and the base are added more than once, in portions and in a stepwise manner, until all of the iodine and the base necessary for the completion of the reaction have been added.

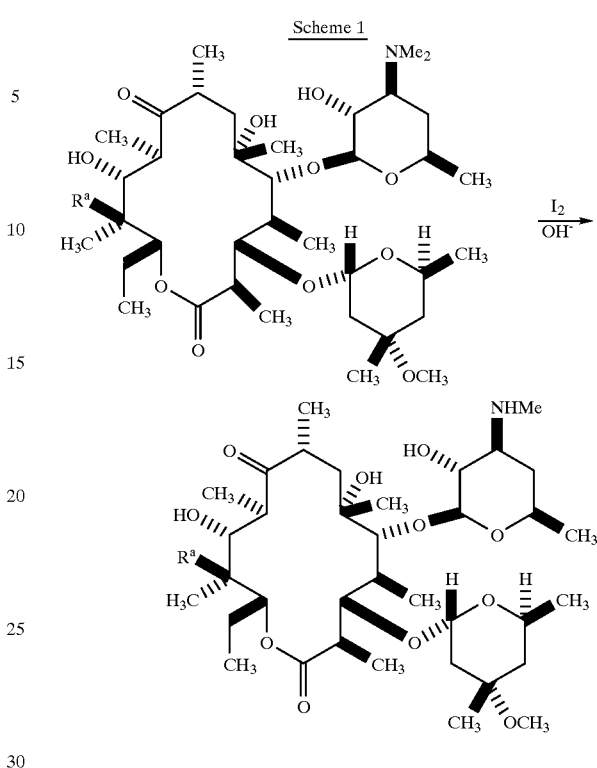

Both the one-stage and the two-stage processes of the invention are carried out in an organic solvent that is capable of at least partially dissolving the reactants. Suitable solvents include methanol, aqueous methanol, dioxane, aqueous dioxane, THF, aqueous THF, DMF and the like, or mixtures thereof. The preferred solvent is methanol or aqueous methanol. The reaction is buffered by addition of sodium acetate. A minimum of 2 equivalents of sodium acetate per equivalent of erythromycin derivative is required, and as many as 15 equivalents may be used. The best results are obtained with about 5 equivalents of sodium acetate.

The reaction is generally carried out at temperatures from about 40° C. to about 70° C., and preferably from about 50° C. to about 60° C. The most preferred temperature is about 55° C., at which maximum yields are obtained.

In the first stage of the two-stage process, a first portion of iodine is added over a period of about fifteen to about sixty minutes. The amounts of iodine that may be added in each portion may vary from 0.25 to 3 equivalents of iodine per equivalent of erythromycin derivative. Preferred portions of iodine are 0.3 to 1.0 equivalents per addition, and the most preferred portion is 0.5 equivalent in the first portion and 0.3 equivalent in subsequent portions. An aqueous base is subsequently added in amounts sufficient to maintain a pH of about 8 to about 9 until the color of iodine disappears. The process is continued with subsequent respective stepwise addition of portions of iodine over a period of another fifteen to sixty minutes followed by additions of an aqueous base as described above until half of the iodine is added.

Suitable aqueous bases for adjusting the pH include sodium hydroxide, sodium carbonate, sodium bicarbonate and the corresponding potassium compounds. The preferred base is sodium hydroxide. Preferred amounts of base are 0.5 to 0.8 equivalents in each portion. At the end of the first stage, the crude product is isolated from the reaction mixture. In the isolation step of the invention, it is generally desirable to remove any residual iodine with the aid of a reducing agent. Suitable reducing agents include sodium thiosulfate, potassium thiosulfate, sodium bisulfite, potassium bisulfite, and the like.

In the second stage of the two-stage process, the crude reaction product is again treated with respective stepwise additions of iodine and an aqueous base as described in the first stage until all of the remaining iodine is added.

The total amount of iodine added in both the stages of the reaction varies from about 1.5 equivalents to about 7.0 equivalents per equivalent of erythromycin derivative. Preferably, the amount of iodine added is from about 1.8 equivalents to about 6.5 equivalents per equivalent of erythromycin derivatives. Generally, about half of the total amount of iodine is added, in about three to about seven stepwise additions, in each stage of the reaction.

In the one-stage process, the reaction is sparged with an inert gas while the respective step-wise additions of iodine and an aqueous base are carried out. In the one-stage process, there is no isolation and re-treatment of the crude product as done in the two-stage process. The advantage obtained from sparging the reaction with an inert gas is believed to be the result of the removal of formaldehyde, a by-product of the reaction, before it can react with the intermediates and produce unwanted impurities. Suitable inert gases include nitrogen, helium and argon, and the most preferred gas is nitrogen.

The total amount of iodine added in the one-stage process varies from about 1.5 equivalents to about 4.0 equivalents per equivalent of erythromycin derivatives. Generally, Iodine is added in about two to about five stepwise additions throughout the process.

The following examples illustrate the process of the invention.

COMPARATIVE EXAMPLE 1

N-demethyl-4"-deoxyerythromycin B was prepared in accordance with the procedure of Example 1 of U.S. Pat. No. 3,725,385.

To a stirred solution of 4"-deoxyerythromycin B (15 g, 21.4 mmol, source Abbott Laboratories) and sodium acetate trihydrate (14.74 g, 107 mmol) in methanol (150 mL) heated to 47° C. was added solid $I_2$ (7.5 g, 30 mmol) in a single portion. To maintain the pH of the mixture in the range of pH 8–9, to this solution was added 1N aqueous NaOH solution in the following amounts and intervals: 6.0 mL at 10 minutes; 6.0 mL at thirty minutes; 3.0 mL at sixty minutes. After three hours the mixture was colorless and poured into water (100 mL) containing 4.5 mL of concentrated ammonium hydroxide. The mixture was extracted with $CHCl_3$ (4×), and the combined organic extracts were washed with dilute ammonium hydroxide solution and dried over $Na_2SO_4$. The solvent was removed, and the residue was crystallized from acetone/concentrated ammonium hydroxide to afford the title compound (58% yield).

EXAMPLE 2

Example 2 illustrates the two-stage process of the invention

2a. Partial conversion of starting material

To a stirred solution of 4"-deoxyerythromycin B (150 g, 214 mmol, source Abbott Laboratories) and sodium acetate trihydrate (165.6 g, 1.2 mol) in methanol (1.5 L) heated to 47° C. was added a first portion of solid $I_2$ (13.6 g, 53.5 mmol) and the mixture was stirred for 25 minutes. A first portion of 1N aqueous NaOH solution (50 mL) was added, and the mixture was stirred until the iodine color disappeared (about 10 minutes). A second portion of solid $I_2$ (13.6 g, 53.5 mmol) was added, and the mixture was stirred for sixty minutes. A second portion of 1N aqueous NaOH solution (50 mL) was added, and the mixture was stirred until the iodine color disappeared (about thirty minutes). A third portion of solid $I_2$ (13.6 g, 53.5 mmol) was added, and the mixture was stirred for thirty minutes. A third portion of 1N aqueous NaOH solution (50 mL) was added, and the mixture was stirred for 3 hours. A fourth portion of solid $I_2$ (13.6 g, 53.5 mmol) was added, and the mixture was stirred for one hour. The reaction was quenched by addition of 10% aqueous sodium thiosulfate solution, and the volume was reduced to ⅓ under vacuum. Isopropyl acetate (2 L) and 500 mL of water were added, and the layers were separated. The organic layer was dried over $MgSO_4$, and the solvent was removed under vacuum. Methanol (150 mL) was added to the residue, and the methanol was removed under vacuum.

2b. Complete conversion of starting material

The residue from step 2a was treated with two portions of iodine and 3 portions of 1N aqueous NaOH solution according to the procedure of step 2a. The starting material was consumed after 5.25 hours of reaction. The reaction was quenched and the product isolated according to the procedures of step 2a to afford the title compound (147 g, 92% yield).

EXAMPLES 3–5

Examples 3–5 illustrate the preparation of N-demethyl-4"-deoxyerythromycin B prepared in accordance with the procedures of Example 2 using varying amounts of the compound (4"-deoxyerythromycin B), at different reaction temperatures and using 5.0 equivalents of sodium acetate instead of the 5.7 equivalents of Example 2. The yields obtained in Example 1–5 are set forth in Table 1 below. The yields of the process of the present invention (Examples 2–5) are very significantly improved over the process of U.S. Pat. No. 3,725,385 (Example 1). The optimum yield of the process of the present invention was obtained at 55° C.

TABLE 1

| Example No. | Compound (g) | 1 N NaOH (mL) | Temperature °C. | Yield (%) |
|---|---|---|---|---|
| 1 | 15 | 15 | 47 | 58 |
| 2 | 150 | 150 | 50 | 92 |
| 3 | 43 | 62 | 50 | 88 |
| 4 | 25 | 80 | 55 | 95 |
| 5 | 25 | 90 | 60 | 85 |

EXAMPLES 6–12

Examples 6–12 illustrate the preparation N-demethyl-4"-deoxyerythromycin B in accordance with the procedure of Example 2 using varying amounts of the compound (4"-deoxyerythromycin B) and various bases as set forth in Table 2 below. The yields of Examples 6–12 are also significantly improved over the process of U.S. Pat. No. 3,725,385 (Example 1 of Table 1).

TABLE 2

| Example No. | Compound (g) | Base Equivalents | Yield (%) |
|---|---|---|---|
| 6 | 3 | NaHCO$_3$, 0.5 eq. per eq. of I$_2$* | 70 |
| 7 | 3 | K$_2$CO$_3$, 2** | 71 |
| 8 | 25 | K$_2$CO$_3$, 2** | 68 |
| 9 | 10 | NaHCO$_3$, 2** | 80 |
| 10 | 3 | NaHCO$_3$, 2*** | 78 |
| 11 | 50 | NaHCO$_3$, 1** | 79 |
| 12 | 10⁻ | NaHCO$_3$, 1** | 80 |

*0.5 equivalents was added at the first addition of I$_2$ (cf. step 2a) and another 0.5 equivalent was added at the beginning of step b.
**1.0 equivalent was added at the first addition of I$_2$ (cf. step 2a) and another 1.0 equivalent was added at the beginning of step b.
***1.0 equivalent was added at the first addition of I$_2$ (cf. step 2a) and another 1.0 equivalent was added at the beginning of step b; also 5 equivalents instead of 5.7 equivalents of sodium acetate were used in step 1.
⁻The starting material was dissolved in a 4:1 mixture of methanol:water.

EXAMPLE 13

Example 13 illustrates the one-stage process of the invention

To a stirred solution of 4"-deoxyerythromycin B (25 g, 35.6 mmol, source Abbott Laboratories) and sodium acetate trihydrate (24.6, 203 mmol) in methanol (312 mL) heated to 55° C. and sparged with nitrogen was added a part of a first portion of solid I$_2$ (4.51 g, 17.8 mmol) and the mixture was stirred for 13 minutes. The remaining part of the first portion of I$_2$ (3.1 g, 12.2 mmol) as well as a first portion of 1N aqueous NaOH solution (30 mL) was added, and the mixture was stirred for 80 minutes. A second portion of solid I$_2$ (3.1 g, 12.2 mmol) was added, as well as a second portion of 1N aqueous NaOH solution (15 mL), and the mixture was stirred for 2.25 hours. A third portion of solid I$_2$ (3.1 g, 12.2 mmol) was added, and the mixture was stirred for thirty minutes. A third portion of 1N aqueous NaOH solution (10 mL) was added, and the mixture was stirred for 1 hour. A fourth portion of solid I$_2$ (13.6 g, 53.5 mmol) was added, and the mixture was stirred for one hour. The pH was adjusted to greater than pH 8 with NaOH after 1 hour and again after two hours. The reaction was quenched after the starting material was consumed (as shown by TLC) by addition of 10% aqueous sodium thiosulfate solution (200 mL), and the volume was reduced to ⅓ under vacuum. Isopropyl acetate (1 L) and 500 mL of 10% NaHCO$_3$ solution were added, and the layers were separated. The organic layer was dried over MgSO$_4$, and the solvent was removed under vacuum. Methanol (50 mL) was added to the residue, and the methanol was removed under vacuum. The product was dried to afford the title compound (98% yield).

It will be understood that the specification and the examples are illustrative and not limitative of the present invention and that other embodiments within the spirit and scope of the invention will suggest themselves to those skilled in the art.

What is claimed is:

1. A two-stage process for the preparation of N-demethyl-4"-deoxyerythromycins A and B, having the formula:

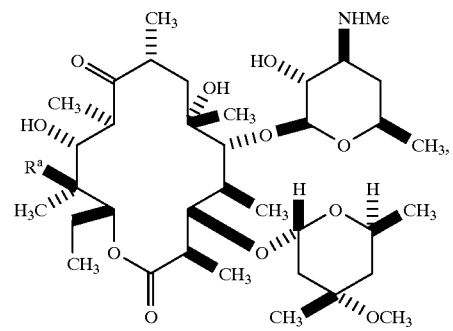

wherein R$^a$ is H or OH, comprising a first stage:

(a) treating a compound having the formula:

wherein R$^a$ is H or OH, in a solution of sodium acetate with stepwise addition, respectively, of iodine and aqueous base in amounts sufficient to maintain a pH of 8–9 in the reaction mixture and stirring until the iodine color disappears, (b) isolating a crude reaction product; and a second stage;

(c) treating the crude reaction product of step (b) in accordance with the step (a) above, and isolating the final product.

2. The process according to claim 1 wherein R$^a$ is H.

3. The process according to claim 1 wherein R$^a$ is OH.

4. The process according to claim 1 wherein the solvent is aqueous methanol and the molar ratio of sodium acetate to that of the compound is in the range of 2 to 15.

5. The process according to claim 1 wherein the amount of I$_2$ added is from about 1.5 to about 7 equivalents per equivalent of the compound.

6. The process according to claim 1 wherein the base is selected from the group consisting of sodium hydroxide, sodium carbonate, sodium bicarbonate, potassium hydroxide, potassium carbonate and potassium bicarbonate.

7. The process according to claim 1 wherein the reaction temperature is from about 40° C. to about 70° C.

8. The process according to claim 6 wherein the reaction temperature is from about 50° C. to about 60° C.

9. The process according to claim 8 wherein the base is sodium hydroxide.

10. The process according to claim 9 wherein the reaction temperature is about 55° C.

11. A one-stage process for the preparation of N-demethyl-4"-deoxyerythromycins A and B, having the formula:

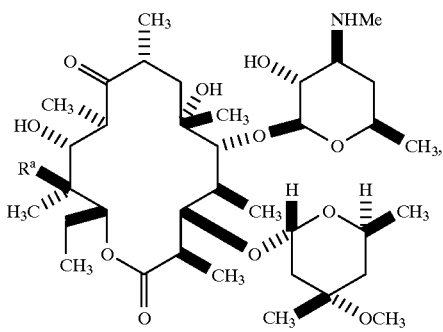

wherein $R^a$ is H or OH, comprising:

(a) treating a compound having the formula:

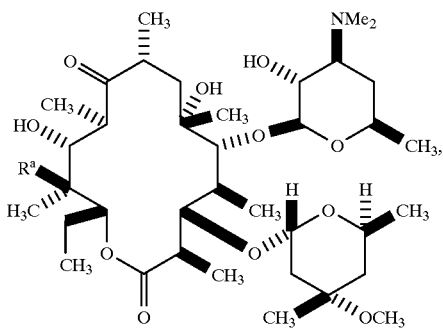

wherein $R^a$ is H or OH, in a solution of sodium acetate accompanied by sparging of the solution with an inert gas, with stepwise addition, respectively, of iodine followed by addition of aqueous base in amounts sufficient to maintain a pH of 8–9 in the reaction mixture and stirring until the iodine color disappears; and (b) isolating the desired product.

12. The process according to claim 11 wherein $R^a$ is H.

13. The process according to claim 11 wherein $R^a$ is OH.

14. The process according to claim 11 wherein the solvent is aqueous methanol and the molar ratio of sodium acetate to that of the compound is in the range of 2 to 15.

15. The process according to claim 11 wherein the amount of iodine is from about 1.5 to about 4 equivalents per equivalent of the compound.

16. The process according to claim 11 wherein the base is selected from the group consisting of sodium hydroxide, sodium carbonate, sodium bicarbonate, potassium hydroxide, potassium carbonate and potassium bicarbonate.

17. The process according to claim 11 wherein the reaction temperature is from about 40° C. to about 70° C.

18. The process according to claim 16 wherein the reaction temperature is from about 50° C. to about 60° C.

19. The process according to claim 18 wherein the base is sodium hydroxide.

20. The process according to claim 19 wherein the reaction temperature is about 55° C.

21. The process according to claim 19 wherein the inert gas is nitrogen.

* * * * *

UNITED STATES PATENT AND TRADEMARK OFFICE
CERTIFICATE OF CORRECTION

PATENT NO. : 5,922,849
DATED : July 13, 1999
INVENTOR(S) : Ramiya H. Premchandran et al.

It is certified that error appears in the above-identified patent and that said Letters Patent is hereby corrected as shown below:

Title page,
Item No. 54, Title -- replace "ERTHROMYCINS" with "ERYTHROMYCINS"

Column 8,
Line 39, replace "stage;" with -- stage: --

Signed and Sealed this

Third Day of July, 2001

*Attest:*

NICHOLAS P. GODICI
*Attesting Officer*    Acting Director of the United States Patent and Trademark Office